United States Patent
Göppel et al.

(10) Patent No.: US 7,204,973 B2
(45) Date of Patent: *Apr. 17, 2007

(54) COSMETIC AND DERMATOLOGICAL LIGHT PROTECTION FORMULATIONS WITH A CONTENT OF HYDROXYBENZOPHENONES AND ALKYLNAPHTHALATES

(75) Inventors: Anja Göppel, Hamburg (DE); Jens Schulz, Schenefeld (DE); Volker Wendel, Frankfurt (DE)

(73) Assignee: Beiersdorf AG, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/500,869

(22) PCT Filed: Nov. 2, 2002

(86) PCT No.: PCT/EP02/12238

§ 371 (c)(1),
(2), (4) Date: Jan. 31, 2005

(87) PCT Pub. No.: WO03/039506

PCT Pub. Date: May 15, 2003

(65) Prior Publication Data

US 2005/0129631 A1    Jun. 16, 2005

(30) Foreign Application Priority Data

Nov. 9, 2001 (DE) ................. 101 55 958

(51) Int. Cl.
| | |
|---|---|
| A61K 8/00 | (2006.01) |
| A61K 8/04 | (2006.01) |
| A61K 31/53 | (2006.01) |
| A61Q 17/00 | (2006.01) |
| A61Q 17/04 | (2006.01) |
| A61Q 19/00 | (2006.01) |

(52) U.S. Cl. .............. 424/59; 424/60; 424/400; 424/401; 514/241

(58) Field of Classification Search ............ 424/59, 424/60, 400, 401; 514/241
See application file for complete search history.

(56) References Cited

U.S. PATENT DOCUMENTS

| | | | |
|---|---|---|---|
| 5,663,213 A | 9/1997 | Jones et al. | |
| 6,355,230 B2 * | 3/2002 | Gers-Barlag et al. | 424/59 |
| 6,368,578 B1 * | 4/2002 | Gers-Barlag et al. | 424/59 |
| 6,409,995 B1 | 6/2002 | Habeck et al. | |
| 6,440,402 B1 * | 8/2002 | Gonzalez et al. | 424/59 |
| 6,491,901 B2 * | 12/2002 | Gers-Barlag et al. | 424/59 |
| 2001/0022966 A1 * | 9/2001 | Gers-Barlag et al. | 424/59 |
| 2001/0026790 A1 * | 10/2001 | Gers-Barlag et al. | 424/59 |
| 2002/0001570 A1 | 1/2002 | Heidenfelder et al. | |

FOREIGN PATENT DOCUMENTS

| | | |
|---|---|---|
| DE | 19917906 | 10/2000 |
| DE | 10008894 | 8/2001 |
| DE | 10008895 | 8/2001 |
| EP | 1133980 | 9/2001 |
| EP | 0761201 | 1/2002 |
| FR | 2801212 | 5/2001 |

OTHER PUBLICATIONS

C. Bonda et al., "A New Photostabilizer for Full Spectrum Sunscreens", Cosmetics & Toiletries, vol. 115, No. 6, 2000, pp. 37-45.

* cited by examiner

Primary Examiner—Shelley A. Dodson
(74) Attorney, Agent, or Firm—Greenblum & Bernstein, P.L.C.

(57) ABSTRACT

The invention relates to light-protective cosmetic or dermatological preparations that contain (a) at least one hydroxybenzophenone, and (b) at last one dialkyl naphthalate of the structural formula (I), wherein $R^1$ and $R^2$ are independently selected form the group of the branched and unbranched alkyl groups that have 6 to 24 carbon atoms. The invention further relates to the use of said formulations

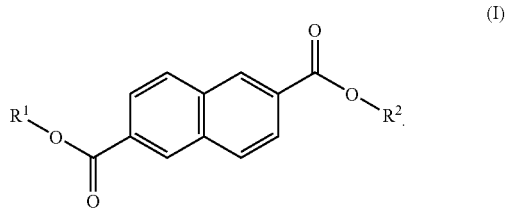

20 Claims, No Drawings

COSMETIC AND DERMATOLOGICAL LIGHT PROTECTION FORMULATIONS WITH A CONTENT OF HYDROXYBENZOPHENONES AND ALKYLNAPHTHALATES

BACKGROUND OF THE INVENTION

1. Field of the Invention

The present invention relates to cosmetic and dermatological light protection preparations.

2. Discussion of Background Information

The harmful effect on the skin of the ultraviolet part of the sun's radiation is generally known. Depending on their respective wavelength, the rays have different effects on the organ skin: so-called UVC radiation, with a wavelength that is less than 290 nm, is absorbed by the ozone layer in the earth's atmosphere and therefore has no physiological significance. In contrast, rays in the range between 290 nm and 320 nm, the so-called UVB range, cause an erythema, a simple sunburn or even more or less severe burns. The narrower range around 308 nm is given as a maximum of the erythema effectiveness of sunlight.

Numerous compounds are known for protection from UVB radiation, which compounds are, e.g., derivatives of 3-benzylidenecamphor, 4-aminobenzoic acid, cinnamic acid, salicylic acid, benzophenone and triazine.

It had long been wrongly assumed that long-wave UVA radiation with a wavelength between 320 nm and 400 nm has only a negligible biological effect. However, it has since been proven through numerous studies that UVA radiation is much more dangerous than UVB radiation with respect to triggering photodynamic, in particular phototoxic, reactions and chronic changes in the skin. The harmful effect of the UVB radiation can also be further increased by UVA radiation.

It is thus proven, that even UVA radiation under quite normal everyday conditions is sufficient to damage within a short time the collagen and elastin fibers that are of substantial importance for the structure and strength of the skin. This causes chronic light-related changes to the skin—the skin "ages" prematurely. The clinical picture of skin aged by light includes, e.g., wrinkles and small lines and an irregular furrowed relief. Furthermore, the parts affected by light-related skin aging can exhibit an irregular pigmentation. Also the formation of brown spots, keratoses and even carcinomas or malignant melanomas is possible. Moreover, skin prematurely aged through everyday UV exposure is characterized by a lower activity of the Langerhans' cells and a slight chronic inflammation.

Approximately 90% of the ultraviolet radiation reaching the earth is composed of UVA rays. Whereas UVB radiation varies greatly depending on numerous factors (e.g., time of year and time of day or degree of latitude), UVA radiation remains relatively constant day to day, regardless of the times of year or times of day or geographical factors. At the same time, most of the UVA radiation penetrates the live epidermis, whereas about 70% of UVB rays are stopped by the horny layer of the epidermis.

It is therefore of fundamental importance for cosmetic and dermatological light protection preparations to provide adequate protection from both UVB and UVA radiation.

In general, the light absorption behavior of light-protection filter substances is very well known and documented, especially as in most industrial nations there are positive lists for the use of such substances that apply rather strict standards for documentation.

However, the use concentration of known light-protection filter substances present as a solid is frequently limited—particularly in combination with other substances to be dissolved. Obtaining higher light protection factors or UVA protective effect thus presents certain difficulties in terms of the technical formulation.

Advantageous UVA filter substances are hydroxybenzophenones, in particular 2-[4'-(diethylamino)-2'-hydroxybenzoyl]benzoic acid hexyl ester (also: aminobenzophenone) which is characterized by the chemical structural formula:

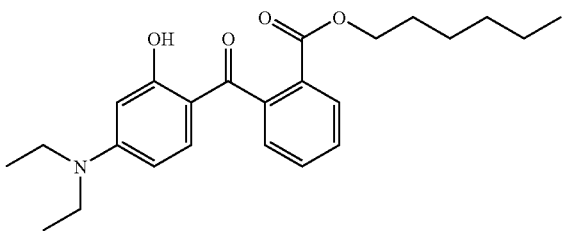

In order to ensure optimum UV protection, these UV filter substances must be present in dissolved form. Hydroxybenzophenones are characterized by a good light-protection effect. However, their main disadvantage is that they are difficult to dissolve in conventional oil components.

Accordingly, one disadvantage of the prior art is that as a rule only comparatively low light-protection factors could be achieved with these filter substances, since their solubility or dispersibility in the formulations is too low, i.e., they cannot be incorporated into such formulations in a satisfactory manner or only with difficulty.

Even if in principle a certain UV protection can be achieved even with limited solubility, another problem often occurs: recrystallization. In particular substances that are difficult to dissolve recrystallize relatively quickly, which can be caused by temperature fluctuations or other influences. However, uncontrolled recrystallization of an essential preparation component such as a UV filter has extremely disadvantageous effects on the properties of the given preparation and—not least—on the light protection aimed for.

SUMMARY OF THE INVENTION

The present invention provides in a simple manner preparations that are characterized by an increased content of hydroxybenzophenones and a correspondingly high UV—in particular UVA—protective effect.

The present invention provides a light-protective cosmetic or dermatological preparation, comprising:
(a) at least one hydroxybenzophenone and
(b) at least one dialkyl naphthalate comprising the structural formula

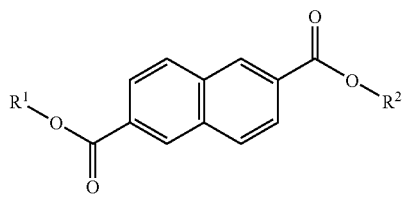

where $R^1$ and $R^2$ are independently branched and unbranched alkyl groups with 6 to 24 carbon atoms.

The present invention also provides a light-protective cosmetic or dermatological preparation, comprising synergistic substance combinations of (a) at least one hydroxybenzophenone, and
(b) at least one dialkyl naphthalate comprising the structural formula

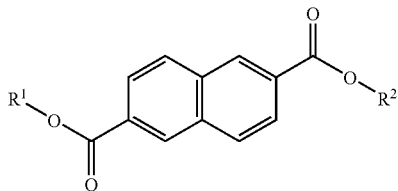

where $R^1$ and $R^2$ are independently branched and unbranched alkyl groups with 6 to 24 carbon atoms,
wherein UV protective effect, in particular UVA protective effect, of the preparation is higher than that of the same preparation that does not contain any substances according to (b).

The at least one dialkyl naphthalate can be present in a range of from 0.001 to 30% by weight—preferably 0.01 to 20% by weight, very particularly preferred 0.5 to 15% by weight, relative to the total weight of the preparation.

The preparation can contain at least one further UV filter substance comprising at least one of triazines, benzotriazoles, liquid UV filter substances and at least one of organic and inorganic pigments.

The preparation can comprise at least one further UVA filter substance and/or a broadband filter comprising at least one of dibenzoylmethane derivatives, in particular 4-(tert.-butyl)-4'-methoxydibenzoylmethane, and 2,4-bis{[4-(2-ethylhexyloxy)-2-hydroxy]phenyl}-6-(4-methoxyphenyl)-1,3,5-triazine.

The preparation can comprise at least one of at least one flavone glycoside, in particular α-glucosylrutin, and vitamin E and/or derivatives thereof.

The present invention is also directed to a method of moistening skin comprising applying a preparation according to the present invention on the skin.

The present invention is also directed to a method of protecting skin against light-related aging of the skin comprising applying a preparation according to the present invention on the skin.

The present invention is also directed to a method of achieving or increasing solubility of at least one hydroxybenzophenone comprising combining the at least one hydroxybenzophenone with at least one dialkyl naphthalate comprising the structural formula

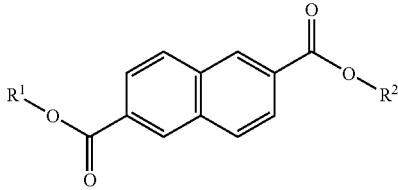

where $R^1$ and $R^2$ are independently branched and unbranched alkyl groups with 6 to 24 carbon atoms.

The present invention is also directed to a method of stabilizing dibenzoylmethane derivatives in cosmetic or dermatological preparations against decomposition that is induced by UV radiation comprising including combinations of (a) at least one hydroxybenzophenone and
(b) at least one dialkyl naphthalate of the structural formula

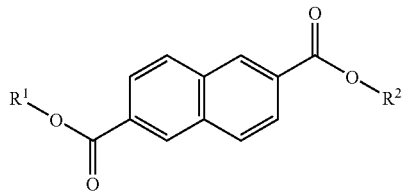

where $R^1$ and $R^2$ are independently branched and unbranched alkyl groups with 6 to 24 carbon atoms,
in a cosmetic or dermatological preparation containing dibenzoylmethane derivatives in an amount effective to stabilize the dibenzoylmethane derivatives against the decomposition that is induced by UV radiation.

DETAILED DESCRIPTION OF THE INVENTION

It was surprising and not foreseeable for one of skill in the art that light-protective cosmetic or dermatological preparations, characterized in that they contain
(a) at least one hydroxybenzophenone and
(b) at least one dialkyl naphthalate that is characterized by the structural formula

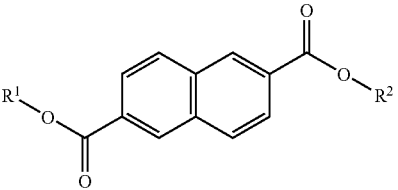

where $R^1$ and $R^2$ are selected independently of one another from the group of branched and unbranched alkyl groups with 6 to 24 carbon atoms, overcome the disadvantages of the prior art.

In addition to one or more oil phases, the preparations within the scope of the present invention may preferably in addition contain one or more aqueous phases and be present, e.g., in the form of W/O, O/W, W/O/W or O/W/O emulsions. Such formulations can preferably also be a micro-emulsion, a solids-emulsion (i.e., an emulsion that is stabilized by solids, e.g., a pickering emulsion), a sprayable emulsion or a hydrodispersion.

In every respect the preparations according to the invention represent extremely satisfactory preparations that are not limited to a restricted selection of raw materials. Accordingly they are particularly suitable for use as the basis for forms of preparation with a variety of uses. The preparations according to the invention show very good sensory and cosmetic properties, such as, e.g., spreadability on the skin or the ability to be absorbed into the skin, and are further characterized by very good light-protection effectiveness with simultaneously excellent skin care data.

Subject matter of the invention therefore also is light-protective cosmetic or dermatological preparations, characterized in that they contain synergistic substance combinations of (a) at least one hydroxybenzophenone and
(b) at least one dialkyl naphthalate that is characterized by the structural formula

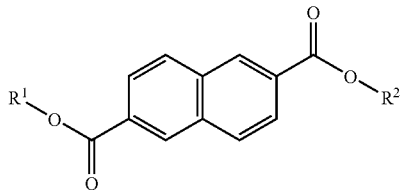

where $R^1$ and $R^2$ are selected independently of one another from the group of
branched and unbranched alkyl groups with 6 to 24 carbon atoms, wherein the UV protective effect, in particular the UVA protective effect, of these preparations is higher than that of the same preparations that do not contain any substances according to (b).

As a rule, the UV protective effect of sunscreen products or the UV filters on which they are based is determined in biological effectiveness tests under standardized conditions. In the sense of the present invention, "UV protective effect" means the protective effect with respect to both UVA radiation and UVB radiation.

Within the scope of the present invention, e.g., the light-protection factor (LSF or SPF) or else IPD values and the like provide a gauge for UV protective effect.

The light-protection factor (LSF, often also called SPF (sun protection factor) indicates the prolongation of the exposure to sunlight that is rendered possible by using the sunscreen product. It is the quotient of erythema threshold time with a sunscreen product and erythema threshold time without a sunscreen product.

The IPD method (IPD=immediate pigment darkening) is normally used to test the UVA protective effect. Like the determination of the light-protection factor, a value is hereby determined that indicates by how much longer the skin protected by the sunscreen product can be irradiated with UVA radiation until the same pigmentation occurs as with unprotected skin.

Another test method that is established throughout Europe is the Australian Standard AS/NZS 2604:1997. The absorption of the preparation in the UVA range is measured thereby. In order to meet the standard, the preparation has to absorb at least 90% of the UVA radiation in the range of 320 to 360 nm.

Subject matter of the invention also is
the use of one or more dialkyl naphthalates that are characterized by the structural formula

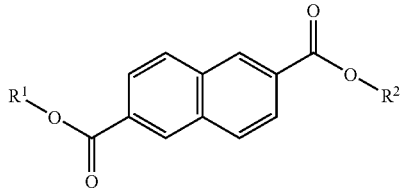

where $R^1$ and $R^2$ are selected independently of one another from the group of branched and unbranched alkyl groups with 6 to 24 carbon atoms to achieve or to increase the solubility of hydroxybenzophenones.

Further advantageous UVA filter substances are, e.g., dibenzoylmethane derivatives, in particular 4-(tert-butyl)-4'-methoxydibenzoylmethane (CAS No. 70356-09-1) which is sold by Givaudan under the trademark Parsol® 1789 and by Merck under the trade name Eusolex® 9020.

The main disadvantage of all dibenzoylmethane derivatives absorbing in the UV range is a certain instability with respect to UV radiation, so that these components are decomposed into inactive products under UV influence and are no longer available for UV absorption. Prior art preparations with a content of these substances therefore expediently also contain certain UV stabilizers, such as, e.g., ethylhexyl-2-cyano-3,3-diphenylacrylate(octocrylene) or 4-methylbenzylidenecamphor. However, it is often desirable to dispense with the use of such UV stabilizers.

It was surprising and not foreseeable for one of skill in the art that the use of substance combinations of
(a) at least one hydroxybenzophenone and
(b) one or more dialkyl naphthalates that are characterized by the structural formula

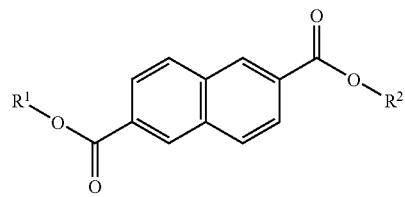

where $R^1$ and $R^2$ are selected independently of one another from the group of branched and unbranched alkyl groups with 6 to 24 carbon atoms for stabilizing dibenzoylmethane derivatives in cosmetic or dermatological preparations against decomposition induced by UV radiation overcome this problem.

It was in particular surprising that with the use according to the present invention it was possible to completely dispense with the use of other UV stabilizers, in particular the use of ethylhexyl-2-cyano-3,3-diphenylacrylate(octocrylene) or 4-methylbenzylidenecamphor.

Hydroxybenzophenones are characterized by the following structural formula:

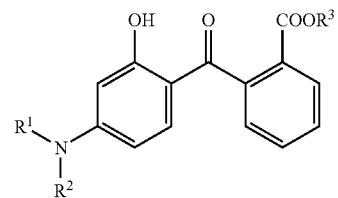

where
$R^1$ and $R^2$ independent of one another are hydrogen, $C_1$–$C_{20}$-alkyl, $C_3$–$C_{10}$-cycloalkyl or $C_3$–$C_{10}$-cyloalkenyl, wherein the substituents $R^1$ and $R^2$ together with the nitrogen atom to which they are bound can form a 5- or 6-ring and
$R^3$ is a $C_1$–$C_{20}$ alkyl radical.

Within the scope of the present invention, a particularly advantageous hydroxybenzophenone is the 2-(4'-diethylamino-2'-hydroxybenzoyl)benzoic acid hexyl ester (also: aminobenzophenone) which is characterized by the following structure:

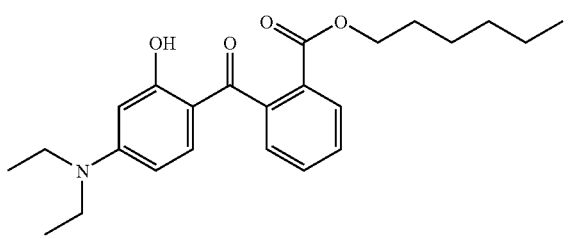

and is available from BASF under the Uvinul A Plus.

According to the invention, cosmetic or dermatological preparations contain 0.1 to 20% by weight, advantageously 0.1 to 15% by weight, very particularly preferred 0.1 to 10% by weight, of one or more hydroxybenzophenones.

Within the scope of the present invention, dialkyl naphthalates for which $R^1$ and/or $R^2$ represent branched alkyl groups with 6 to 10 carbon atoms are advantageous. Within the scope of the present invention diethylhexyl naphthalate is very particularly preferred which is available, e.g., under the trade name Hallbrite TQ™ from CP Hall or Corapan TQ™ from H&R.

According to the invention cosmetic or dermatological preparations advantageously contain 0.001 to 30% by weight, preferably 0.01 to 20% by weight, very particularly preferred 0.5 to 15% by weight, of one or more dialkyl naphthalates.

The cosmetic or dermatological light-protection formulations according to the invention can be composed as usual and be used for cosmetic or dermatological light-protection, furthermore for the treatment, care and cleansing of the skin and/or hair and as a cosmetic product in decorative cosmetics.

According to their constitution, cosmetic or topical dermatological preparations within the scope of the present invention can be used, e.g., as skin protective cream, cleansing milk, day or night cream, etc. It is optionally possible and advantageous to use the compositions according to the invention as base for pharmaceutical formulations.

For application the cosmetic and dermatological preparations are applied to the skin and/or the hair in sufficient quantity in the manner usual for cosmetics.

The cosmetic and dermatological preparations according to the invention may contain cosmetic auxiliary ingredients, as normally used in such preparations, e.g., preservatives, preservative aids, bactericides, perfumes, substances to prevent foaming, dyes, pigments that have a coloring effect, thickeners, moisturizers and/or humectants, fillers that improve the feel of the skin, fats, oils, waxes or other customary components of a cosmetic or dermatological formulation, such as alcohols, polyols, polymers, foam stabilizers, electrolytes, organic solvents or silicone derivatives.

Advantageous preservatives within the scope of the present invention are, e.g., formaldehyde releasing agents (such as, e.g., DMDM hydantoin which is available, e.g., under the trade name Glydant™ from Lonza), iodopropylbutyl carbamate (e.g., available from Lonza under the trade names Glycacil-L, Glycacil-S and/or Dekaben LMB from Jan Dekker), parabens (i.e., p-hydroxybenzoic acid alkyl esters, such as methyl, ethyl, propyl and/or butyl paraben), phenoxyethanol, ethanol, benzoic acid and the like. Usually the preservative system according to the invention further advantageously also includes preservative aids, such as, e.g., octoxyglycerin, glycine soy, etc.

Particularly advantageous preparations are further obtained if antioxidants are used as additional or active substances. According to the invention, the preparations advantageously contain one or more antioxidants. As favorable antioxidants that are nevertheless to be used optionally, all antioxidants suitable or usual for cosmetic and/or dermatological applications can be used.

Water-soluble antioxidants, such as, e.g., vitamins, e.g., ascorbic acid and its derivatives, may be used particularly advantageously within the scope of the present invention.

Preferred antioxidants are furthermore vitamin E and its derivatives and vitamin A and its derivatives.

The quantity of the antioxidants (one or more compounds) in the preparations is preferably 0.001 to 30% by weight, particularly preferred 0.05 to 20% by weight, in particular 0.1 to 10% by weight, relative to the total weight of the preparation.

If vitamin E and/or its derivatives represent the antioxidant(s), it is advantageous to select their respective concentrations from the range from 0.001 to 10% by weight, relative to the total weight of the formulation.

If vitamin A or vitamin A derivatives or carotenes or their derivatives represent the antioxidant(s), it is advantageous to select their respective concentrations from the range from 0.001 to 10% by weight relative to the total weight of the formulation.

It is in particular advantageous for the cosmetic preparations according to the present invention to contain cosmetic or dermatological active substances, where preferred active substances are antioxidants that can protect the skin from oxidative stress.

Further advantageous active substances within the scope of the present invention are natural active substances and/or their derivatives, such as, e.g., alpha-lipoic acid, phytoen, D-biotin, coenzyme Q10alpha-glucosylrutin, carnitine, carnosine, natural and/or synthetic isoflavonoids, creatine, taurine and/or β-alanine.

Formulae according to the invention which contain, e.g., known anti-wrinkle active substances, such as flavone glycosides (in particular α-glycosylrutin), coenzyme Q10vitamin E and/or derivatives and the like are in particular advantageous for prophylaxis and treatment of cosmetic or dermatological skin changes, such as occur, e.g., with aging of the skin (such as, e.g., dryness, roughness and formation of dryness wrinkles, itching, reduced regreasing (e.g., after washing), visible vasodilatation (telangiectases, cuperosis), flabbiness and the formation of wrinkles and small lines, local hyperpigmentation, hypopigmentation and defective pigmentation (e.g., senile keratoses), increased susceptibility to mechanical stress (e.g., chapping) and the like). They are also advantageously suitable for preventing the appearance of dry or rough skin.

The aqueous phase of the preparations according to the invention can advantageously contain customary cosmetic additives, such as alcohols, in particular those with a low C number, preferably ethanol and/or isopropanol, diols or polyols with a low C number and their ethers, preferably propylene glycol, glycerin, ethylene glycol, ethylene glycol monoethyl ether or ethylene glycol monobutyl ether, propylene glycol monomethyl ether, propylene glycol monoethyl ether or propylene glycol monobutyl ether, diethylene glycol monomethyl ether or diethylene glycol monoethyl ether and analogous products, polymers, foam stabilizers, electrolytes and in particular one or more thickeners which can be advantageously selected from the group silicon dioxide, aluminum silicates, polysaccharides or their derivatives, e.g., hyaluronic acid, xanthan gum, hydroxypropyl methyl cellulose, particularly advantageously from the group of polyacrylates, preferably a polyacrylate from the group of so-called carbopols, e.g., carbopols of types 980, 981, 1382, 2984, 5984, each individually or in combination. Moisturizers can also preferably be used.

Substances or substance mixtures that give cosmetic or dermatological preparations the property after application or distribution on the skin surface of reducing the moisture loss of the horny layer of the epidermis (also called transepidermal water loss (TEWL)) and/or favorably influence the hydration of the horny layer of the epidermis, are called moisturizers.

Within the scope of the present invention, advantageous moisturizers are, e.g., glycerin, lactic acid and/or lactates, in particular sodium lactate, butylene glycol, propylene glycol, biosaccharide gum-1glycine soy, ethylhexyloxyglycerin, pyrrolidone carboxylic acid and urea. It is furthermore advantageous to use polymeric moisturizers from the group of polysaccharides that are water-soluble and/or can be swelled in water and/or can be gelled with the aid of water. Particularly advantageous, e.g., are hyaluronic acid, chitosan and/or a fucose-rich polysaccharide which is filed in the Chemical Abstracts under registration number 178463-23-5 and is available, e.g., under the name Fucogel® 1000 from SOLABIA S.A.

The cosmetic or dermatological preparations according to the invention can further advantageously, although not mandatorily, contain fillers that, e.g., further improve the sensory and cosmetic properties of the formulations and, e.g., cause or intensify a velvety or silky feel of the skin. Advantageous fillers within the scope of the present invention are starch and starch derivatives (such as, e.g., tapioca starch, distarch phosphate, aluminum or sodium starch octenylsuccinate and the like), pigments that neither have mainly a UV filter effect nor have mainly a coloring effect (such as, e.g., boron nitride, etc.) and/or Aerosils® (CAS No. 7631-86-9).

The oil phase of the formulations according to the invention is advantageously selected from the group of polar oils, e.g., from the group of lecithins and fatty acid triglycerides, namely the triglycerin esters of saturated and/or unsaturated branched and/or unbranched alkanecarboxylic acids with a chain length of 8 to 24, in particular 12 to 18 C-atoms. The fatty acid triglycerides can be advantageously selected, e.g., from the group of synthetic, semi-synthetic and natural oils, such as, e.g., cocoglyceride, olive oil, sunflower oil, soybean oil, peanut oil, rapeseed oil, almond oil, palm oil, coconut oil, castor oil, wheat germ oil, grape-seed oil, thistle oil, evening primrose oil, macadamia nut oil and the like.

According to the invention, e.g., natural waxes of animal and plant origin, such as, e.g., beeswax and other insect waxes and berry wax, shea butter and/or lanolin (wool wax) are furthermore advantageous.

Within the scope of the invention, other advantageous polar oil components can further be selected from the group of esters of saturated and/or unsaturated, branched and/or unbranched alkanecarboxylic acids with a chain length of 3 to 30 C-atoms and saturated and/or unsaturated branched and/or unbranched alcohols with a chain length of 3 to 30 C-atoms and from the group of esters of aromatic carboxylic acids and saturated and/or unsaturated, branched and/or unbranched alcohols with a chain length of 3 to 30 C-atoms. Such ester oils can then be advantageously selected from the group octyl palmitate, octyl cocoate, octyl isostearate, octyldodecyl myristate, octyl dodecanol, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and synthetic, semi-synthetic and natural mixtures of such esters, such as, e.g., jojoba oil.

Furthermore, the oil phase can advantageously be selected from the group of dialkyl ethers and dialkyl carbonates; e.g., dicaprylyl ether (Cetiol OE) and/or dicaprylyl carbonate, e.g., the one available from Cognis under the trade name Cetiol CC, are advantageous.

It is furthermore preferred to select the oil component(s) from the group isoeicosane, neopentyl glycol diheptanoate, propylene glycol dicaprylate/dicaprate, caprylic/capric/diglyceryl succinate, butylene glycol dicaprylate/dicaprate, $C_{12\text{-}13}$ alkyl lactate, di-$C_{12\text{-}13}$ alkyl tartrate, triisostearin, dipentaerythrityl hexacaprylate/hexacaprate, propylene glycol monoisostearate, tricaprylin, dimethyl isosorbide. It is particularly advantageous if the oil phase of the formulations according to the invention has a content of $C_{12\text{-}15}$ alkyl benzoate or completely consists thereof.

Further advantageous oil components are, e.g., butyl octyl salicylate (e.g., the one available from CP Hall under the trade name Hallbrite BHB), hexadecyl benzoate and butyloctyl benzoate and mixtures thereof (Hallstar AB).

Any desired mixtures of such oil and wax components can also be used advantageously within the scope of the present invention.

Furthermore, the oil phase can likewise advantageously also contain nonpolar oils, e.g., those that are selected from the group of branched and unbranched hydrocarbons and waxes, in particular mineral oil, Vaseline (petrolatum), paraffin oil, squalane and squalene, polyolefins, hydrogenated polyisobutenes and isohexadecane. Among the polyolefins, polydecenes are the preferred substances.

The oil phase can furthermore advantageously have a content of cyclic or linear silicone oils or it can consist completely of such oils, whereby, however, the use of an additional content of other oil phase components, apart from the silicone oil or silicone oils, is preferred.

Silicone oils are high molecular weight synthetic polymeric compounds in which silicon atoms are linked via oxygen atoms in a chain-like or net-like manner and the remaining valences of the silicon are saturated by hydrocarbon radicals (mostly methyl groups, more rarely ethyl groups, propyl groups, phenyl groups, i.a.). The silicone oils are systematically termed polyorganosiloxanes. The methyl-substituted polyorganosiloxanes, which represent the quantitatively most significant compounds of this group and are characterized by the following structural formula.

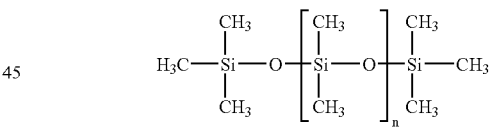

are also called polydimethylsiloxane or dimethicone (INCI). Dimethicones are available in different chain lengths or with different molecular weights.

Within the scope of the present invention, particularly advantageous polyorganosiloxanes are, e.g., dimethylpolysiloxanes[poly(dimethylsiloxane)], which are available, e.g., under the trade names Abil 10 through 10 000 from Th. Goldschmidt. Phenylmethylpolysiloxanes (INCI: phenyl dimethicone, phenyl trimethicone), cyclic silicones (octamethylcyclotetrasiloxane or decamethylcyclopentasiloxane), which according to the INCI are also called cyclomethicones, amino-modified silicones (INCI: amodimethicone) and silicone waxes, e.g., polysiloxane/polyalkylene copolymers (INCI: stearyl dimethicone and cetyl dimethicone) and dialkoxydimethylpolysiloxanes (stearoxy dimethicone and behenoxy stearyl dimethicone) which are available from Th. Goldschmidt as various Abil wax types, are also advantageous. However, other silicone oils can also be advantageously used within the scope of the present invention, e.g., cetyl dimethicone, hexamethylcyclotrisiloxane, polydimethylsiloxane, poly(methylphenylsiloxane).

Within the scope of the present invention, it is also advantageous to produce cosmetic and dermatological preparations, the main purpose of which is not protection from sunlight, but which nevertheless contain a content of further UV protective substances. Thus UVA or UVB filter substances are usually incorporated, e.g., into day creams or makeup products. UV protective substances, just like antioxidants and, if desired, preservatives, represent an effective protection of the preparations themselves from spoilage. Furthermore, cosmetic and dermatological preparations are favorable that are present in the form of a sunscreen product.

Accordingly, the preparations within the scope of the present invention preferably contain at least one further UVA, UVB and/or broadband filter substance. Although not necessary, the formulations can also optionally contain one or more organic and/or inorganic pigments as UV filter substances which can be present in the aqueous phase and/or the oil phase.

Furthermore, the preparations according to the invention can also advantageously be present in the form of so-called oil-free cosmetic or dermatological emulsions which contain an aqueous phase and at least one UV filter substance liquid at room temperature and/or one or more silicone derivatives as a further phase. Within the scope of, the present invention, oil-free formulations can also advantageously contain further lipophilic components, such as, e.g., lipophilic active substances.

Within the scope of the present invention, particularly advantageous UV filter substances that are liquid at room temperature are homomenthyl salicylate (INCI: homosalate), 2-ethylhexyl-2-cyano-3,3-diphenylacrylate (INCI: octocrylene), 2-ethylhexyl-2-hydroxybenzoate (2-ethylhexyl salicylate, INCI: octyl salicylate) and esters of cinnamic acid, preferably 4-methoxycinnamic acid (2-ethylhexyl)ester (2-ethylhexyl-4-methoxycinnamate, INCI: octyl methoxycinnamate) and 4-methoxy cinnamic acid isopentyl ester(isopentyl-4-methoxycinnamate, INCI: isoamyl p-methoxycinnamate).

Preferred inorganic pigments are metal oxides and/or other metal compounds that are hardly soluble or insoluble in water, in particular oxides of titanium ($TiO_2$), zinc (ZnO), iron (e.g., $Fe_2O_3$), zirconium ($ZrO_2$), silicon ($SiO_2$), manganese (e.g., MnO), aluminum ($Al_2O_3$), cerium (e.g., $Ce_2O_3$), mixed oxides of the corresponding metals and mixtures of such oxides and the sulfate of barium ($BaSO_4$).

Within the scope of the present invention, the pigments can also be used advantageously in the form of commercially available oily or aqueous predispersions. Dispersion aids and/or solubilizers can advantageously be added to these predispersions.

According to the invention the pigments can be advantageously surface-treated ("coated") whereby, e.g., a hydrophilic, amphiphilic or hydrophobic character is to be formed or should be retained. This surface treatment can consist in providing the pigments with a thin hydrophilic and/or hydrophobic inorganic and/or organic layer according to methods that are known per se. Within the scope of the present invention, the different surface coatings can also contain water.

Inorganic surface coatings within the scope of the present invention can be composed of aluminum oxide ($Al_2O_3$), aluminum hydroxide $Al(OH)_3$, or aluminum oxide hydrate (also: alumina, CAS No.: 1333-84-2), sodium hexametaphosphate $(NaPO_3)_6$, sodium metaphosphate $(NaPO_3)_n$, silicon dioxide ($SiO_2$) (also silica, CAS No.: 7631-86-9) or iron oxide ($Fe_2O_3$). These inorganic surface coatings can be present individually, in combination and/or in combination with organic coating materials.

Within the scope of the present invention, organic surface coatings can comprise vegetable or animal aluminum stearate, vegetable or animal stearic acid, lauric acid, dimethylpolysiloxane (also: dimethicone), methylpolysiloxane (methicone), simethicone (a mixture of dimethylpolysiloxane with an average chain length of 200 to 350 dimethylsiloxane units and silica gel) or alginic acid. These organic surface coatings can be present individually, in combination and/or in combination with inorganic coating materials.

Zinc oxide particles and predispersions of zinc oxide particles suitable according to the invention are available under the following trade names from the listed companies:

| Trade Name | Coating | Manufacturer |
|---|---|---|
| Z-Cote HP1 | 2% dimethicone | BASF |
| Z-Cote | / | BASF |
| ZnO NDM | 5% dimethicone | H&R |

Suitable titanium dioxide particles and predispersions of titanium dioxide particles are available under the following trade names from the listed companies:

| Trade Name | Coating | Manufacturer |
|---|---|---|
| MT-100TV | Aluminum hydroxide/stearic acid | Tayca Corporation |
| MT-100Z | Aluminum hydroxide/stearic acid | Tayca Corporation |
| Eusolex T-2000 | Alumina/simethicone | Merck KgaA |
| Titandioxid T805 (Uvinul $TiO_2$) | Octyl trimethylsilane | Degussa |
| Tioveil AQ 10PG | Alumina/silica | Solaveil/Uniquema |

Further advantageous pigments are latex particles. Latex particles that are advantageous according to the invention are those described in the following documents: U.S. Pat. No. 5,663,213 and EP 0 761 201, respectively. Latex particles that are particularly advantageous are those that are made up of water and styrene/acrylate copolymers and are available, e.g., under the trade name "Alliance SunSphere" from Rohm & Haas.

Advantageous UVA filter substances within the scope of the present invention are dibenzoylmethane derivatives, in particular 4-(tert-butyl)-4'-methoxydibenzoylmethane (CAS No. 70356-09-1) which is sold by Givaudan under the trademark Parsol® 1789 and by Merck under the trade name Eusolex® 9020.

Advantageous further UV filter substances within the scope of the present invention are sulfonated water-soluble UV filters, such as, e.g.:

Phenylene-1,4-bis(2-benzimidazyl)-3,3'-5,5'-tetrasulfonic acid and its salts, in particular the corresponding sodium, potassium or triethanolammonium salts, in particular the phenylene-1,4-bis(2-benzimidazyl)-3,3'-5,5'-tetrasulfonic acid-bis-sodium salt with the INCI name bisimidazylate (INCI no.: 180898-37-7) which is available, e.g., under the trade name Neo Haliopan AP from Haarmann & Reimer;

Salts of the 2-phenylbenzimidazole-5-sulfonic acid, such as its sodium, potassium or triethanolammonium salt, and the sulfonic acid itself with the INCI name phenylbenzimidazole sulfonic acid (CAS. No. 27503-81-7) which is available, e.g., under the trade name Eusolex 232 from Merck or under Neo Heliopan Hydro from Haarmann & Reimer;

1,4-di(2-oxo-10-sulfo-3-bornylidenemethyl)benzene (also: 3,3'-(1,4-phenylene-dimethylene)-bis(7,7-dimethyl-2-oxo-bicyclo-[2.2.1]hept-1-ylmethane-sulfonic acid) and its salts (in particular the corresponding 10-sulfato compounds, in particular the corresponding sodium, potassium or triethanolammonium salt), which is also known as benzene-1,4-di(2-oxo-3-bornylidenemethyl-10-sulfonic acid). Benzene-1,4-di(2-oxo-3-bornylidenemethyl-10-sulfonic acid) has the INCI name terephthalidene dicamphorsulfonic acid. (CAS.-No. 90457-82-2) and is available, e.g., under the trade name Mexoryl SX from Chimex;

Sulfonic acid derivatives of 3-benzylidenecamphor, such as, e.g., 4-(2-oxo-3-bornylidenemethyl)benzenesulfonic acid, 2-methyl-5-(2-oxo-3-bornylidenemethyl)sulfonic acid and their salts.

Advantageous UV filter substances within the scope of the present invention are furthermore so-called broadband filters, i.e., filter substances which absorb both UVA and UVB radiation.

Advantageous broadband filters or UVB filter substances are, e.g., triazine derivatives, such as, e.g.:

2,4-bis{[4-(2-ethylhexyloxy)-2-hydroxy]phenyl}-6-(4-methoxyphenyl)-1,3,5-triazine (INCI: methylene bis-benzotriazole methylbutylphenol), which is available under the trade name Tinosorb® S from CIBA-Chemikalien GmbH;

Dioctylbutylamidotriazone (INCI: diethylhexyl butamidotriazone), which is available under the trade name UVASORB HEB from Sigma 3V;

4,4',4''-(1,3,5-triazine-2,4,6-triyltriimino)-tris-benzoic acid-tris(2-ethylhexyl ester), also: 2,4,6-tris[anilino-(p-carbo-2'-ethyl-1'-hexyloxy)]-1,3,5-triazine (INCI: octyl triazone), which is sold by BASF Aktiengesellschaft under the trade name UVINUL® T 150.

Within the scope of the present invention, an advantageous broadband filter is also 2,2'-methylene-bis(6-(2H-benzotriazol-2-yl)-4-(1,1,3,3-tetramethylbutyl)phenol), (INCI: bisoctyltriazole) which is available under the trade name Tinosorb® M from CIBA-Chemikalien GmbH.

An advantageous broadband filter within the scope of the present invention is also 2-(2H-benzotriazol-2-yl)-4-methyl-6-[2-methyl-3-[1,3,3,3-tetramethyl-1-[(trimethyl-silyl)oxy] disiloxanyl]propyl]phenol (CAS -No. 155633-54-8) with the INCI name of drometrizole trisiloxane.

The further UV filter substances can be oil-soluble. Advantageous oil-soluble filter substances are, e.g.:

3-benzylidenecamphor derivatives, preferably 3-(4-methylbenzylidene)camphor, 3-benzylidenecamphor;

4-aminobenzoic acid derivatives, preferably (2-ethylhexyl) 4-(dimethylamino)benzoate, amyl 4-(dimethylamino)benzoate;

Derivatives of benzophenone, preferably 2-hydroxy-4-methoxybezophenone, 2-hydroxy-4-methoxy-4'-methylbenzophenone, 2,2'-dihydroxy-4-methoxybenzophenone, (3-(4-(2,2-bis ethoxycarbonylvinyl)phenoxy)propenyl) methylsiloxane-/dimethylsiloxane copolymer which is available, for example, under the trade name Parsol SLX® from Hoffmann La Roche, and UV filters bound to polymers.

A further light protection filter substance which can be used advantageously according to the invention is ethylhexyl-2-cyano-3,3-diphenyl acrylate(octocrylene), which is available from BASF under the name Uvinul® N 539.

Particularly advantageous preparations within the scope of the present invention that are characterized by a high or very high UVA protection, preferably contain in addition to the filter substance(s) according to the invention furthermore further UVA and/or broadband filters, in particular dibenzoylmethane derivatives [e.g., 4-(tert-butyl)-4'-methoxydibenzoylmethane] and/or 2,4-bis{[4-(2-ethylhexyloxy)-2-hydroxy]phenyl}-6-(4-methoxyphenyl)-1,3,5-triazine, each individually or in any combination with one another.

Of course, the list of specified UV filters that can be used within the scope of the present invention is not intended to be limiting.

The preparations according to the invention advantageously contain the substances that absorb UV radiation in the UVA and/or UVB range, in a total amount of, e.g., 0.1% by weight to 30% by weight, preferably 0.5 to 20% by weight, in particular 1.0 to 15.0% by weight, each relative to the total weight of the preparations, in order to provide cosmetic preparations that protect the hair or the skin from the entire range of ultraviolet radiation.

Furthermore, it can optionally be advantageous to incorporate film-formers into the cosmetic or dermatological preparations according to the invention, e.g., in order to improve the hygrostability of the preparations or to increase the UV protective effect (UVA and/or UVB boosting). Water-soluble or dispersible as well as fat-soluble film-formers are suitable, each individually or in combination with one another.

Advantageous water-soluble or dispersible film-formers are, e.g., polyurethanes (e.g., the Avalure® types from Goodrich), dimethicone copolyol polyacrylate (Silsoft Surface® from the Witco Organo Silicones Group), PVP/NVA (VA=vinyl acetate) copolymer (Luviscol VA 64 Powder from BASF), etc.

Advantageous fat-soluble film-formers are, e.g., the film-formers from the group of polymers based on polyvinylpyrrolidone (PVP)

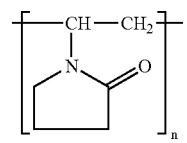

Copolymers of polyvinylpyrrolidone are particularly preferred, e.g., the PVP hexadecene copolymer and the PVP eicosene copolymer, which are available under the trade names Antaron V216 and Antaron V220 from GAF Chemicals Corporation, and Tricontayl PVP, and the like.

The following examples are to illustrate the present invention without limiting it. The numbers in the examples refer to percentages by weight relative to the total weight of the respective preparations.

EXAMPLES

| | 1. O/W Sunscreen Emulsions | | | | | | |
|---|---|---|---|---|---|---|---|
| | 1 | 2 | 3 | 4 | 5 | 6 | 7 |
| Glycerin monostearate SE | 0.50 | 1.00 | 3.00 | | | 1.50 | |
| Glyceryl stearate citrate | 2.00 | | | 1.00 | 2.00 | | 4.00 |
| Stearic acid | | 3.00 | | 2.00 | | | |
| PEG-40 stearate | 0.50 | | | | | 2.00 | |
| Cetyl phosphate | | | | | 1.00 | | |
| Cetearyl sulfate | | | | | | 0.75 | |
| Stearyl alcohol | | | 3.00 | | | 2.00 | 0.50 |
| Cetyl alcohol | 2.50 | 1.00 | | 1.50 | 0.50 | | 2.00 |
| Aminobenzophenone | 2.00 | 1.50 | 0.75 | 1.00 | 2.00 | 4.50 | 5.00 |
| Ethylhexyl methoxycinnamate | | | | 5.00 | 6.00 | | 8.00 |
| Bis-ethylhexyloxyphenol methoxyphenyl triazine | | 1.50 | | 2.00 | 2.50 | | 2.50 |
| Butyl methoxydibenzoylmethane | | | 2.00 | | | 2.00 | 1.50 |
| Disodium phenyl-dibenzimidazole tetrasulfonate | 2.50 | | 0.50 | 2.00 | | | 0.30 |
| Ethylhexyl triazone | 4.00 | | 3.00 | 4.00 | | 2.00 | |
| Octocrylene | | 4.00 | | | | | 7.50 |
| Diethylhexyl butamido triazone | 1.00 | | | 2.00 | 1.00 | | 1.00 |
| Phenylbenzimidazole sulfonic acid | 0.50 | | | 3.00 | | | |
| Methylene bis-benzotriazolyl tetramethylbutyl phenol | 2.00 | | 0.50 | 1.50 | 2.50 | | |
| Ethylhexyl salicylate | | | 3.00 | | | | 5.00 |
| Drometrizole trisiloxane | | | 0.5 | | | 1.00 | |
| Terephthalidene dicamphorsulfonic acid | | 1.50 | | | 1.00 | 0.50 | |
| Diethylhexyl-2,6-naphthalate | 3.50 | 4.00 | 7.00 | 9.50 | 6.70 | 5.50 | 10.00 |
| Titanium dioxide MT-100Z | 1.00 | | | 3.00 | 2.00 | | 1.50 |
| Zinc oxide HP1 | | | | 0.25 | | 2.00 | |
| C12–15 Alkyl benzoate | | 2.50 | | | 4.00 | 7.00 | |
| Dicaprylyl ether | | | 3.50 | | 2.00 | | |
| Butylene glycol dicaprylate/dicaprate | 5.00 | | | 6.00 | | | |
| Dicaprylyl carbonate | | | 6.00 | | | 2.00 | |
| Cocoglycerides | 4.50 | 7.50 | | | 3.00 | | |
| Dimethicone | | 0.50 | 1.00 | | 2.00 | | |
| Cyclomethicone | 2.00 | | | 0.50 | | | 0.50 |
| Shea butter | | 2.00 | | | | | |
| PVP hexadecene copolymer | 0.50 | | | 0.50 | 1.00 | | 1.00 |
| Glycerin | 3.00 | 7.50 | | 7.50 | 5.00 | | 2.50 |
| Xanthan gum | 0.15 | | 0.05 | | | | 0.30 |
| Sodium carbomer | | 0.20 | 0.10 | 0.20 | | | |
| Vitamin E acetate | 0.50 | | 0.25 | | 0.75 | | 1.00 |
| Fucogel ® 1000 | | 3.50 | 10.00 | | | | |
| Glycine soy | | | | 0.50 | | 1.50 | 1.00 |
| Ethylhexyl oxyglycerin | 0.35 | | | | | | 0.75 |
| DMDM hydantoin | | 0.60 | 0.40 | 0.20 | | | |
| Glycacil -L ® | | | | 0.18 | 0.20 | | |
| Methylparaben | 0.15 | | 0.25 | | 0.50 | | |
| Phenoxyethanol | 1.00 | 0.40 | | 0.40 | 0.50 | 0.40 | |
| Trisodium EDTA | 0.02 | | 0.05 | | | | |
| Iminodisuccinic acid | | | | 0.25 | 1.0 | | |
| Ethanol | | 2.00 | 1.50 | | 3.00 | 4.50 | 5.00 |
| Perfume | 0.10 | 0.20 | 0.35 | | | 0.40 | 0.20 |
| Water | ad 100 | ad 100 | ad 100 | ad 100 | ad 100 | ad 100 | ad 100 |

| 2. Hydrodispersions | | | | | |
|---|---|---|---|---|---|
| | 1 | 2 | 3 | 4 | 5 |
| Ceteareth-20 | 1.00 | | | 0.5 | |
| Cetyl alcohol | | | 1.00 | | |
| Sodium carbomer | | 0.20 | | 0.30 | |
| Acrylates/C10–30 alkyl acrylate crosspolymer | 0.50 | | 0.40 | 0.10 | 0.50 |
| Xanthan gum | | 0.30 | 0.15 | | 0.50 |
| Aminobenzophenone | 2.50 | 3.00 | 1.00 | 0.50 | 1.50 |
| Ethylhexyl methoxycinnamate | | | | 5.00 | 8.00 |
| Bis-ethylhexyloxyphenol methoxyphenyl triazine | | 1.50 | | 2.00 | 2.50 |
| Butyl methoxydibenzoylmethane | | 0.50 | | 3.00 | 2.50 |
| Disodium phenyl-dibenzimidazole tetra-sulfonate | 0.50 | | | | 3.00 |
| Ethylhexyl triazone | 4.00 | | 3.00 | | 1.00 |
| Octocrylene | | 4.00 | 3.90 | | 6.50 |
| Diethylhexyl butamidotriazone | 1.00 | | | 2.00 | |
| Phenylbenzimidazole sulfonic acid | 0.50 | | | 3.00 | |
| Methylene bis-benzotriazolyl tetramethylbutyl phenol | 2.50 | 0.50 | | | |
| Drometrizole trisiloxane | | | 1.00 | | 1.50 |
| Terephthalidene dicamphorsulfonic acid | | 0.50 | | | 1.00 |
| Diethylhexyl-2,6-naphthalate | 10.00 | 8.00 | 7.50 | 5.50 | 9.80 |
| Titanium dioxide MT-100TV | 0.50 | | 2.00 | | 1.00 |
| Zinc oxide HP1 | | | 1.00 | 2.00 | 3.00 |
| C12–15 Alkyl benzoate | 2.00 | 2.50 | | | |
| Dicaprylyl ether | | 4.00 | | | |
| Butyleneglycol dicaprylate/dicaprate | 4.00 | | 2.00 | 6.00 | |
| Dicaprylyl carbonate | | 2.00 | 6.00 | | |
| Dimethicone | | 0.50 | 1.00 | | |
| Phenyl trimethicone | 2.00 | | | 0.50 | |
| Shea butter | | 2.00 | | 5.00 | |
| PVP hexadecene copolymer | 0.50 | | | 0.50 | 1.00 |
| Tricontanyl PVP | 0.50 | | 1.00 | | |
| Ethylhexyl glycerin | | | 1.00 | | 0.80 |
| Glycerin | 3.00 | 7.50 | | 7.50 | 8.50 |
| Glycine soy | | | 1.50 | | 1.00 |
| Vitamin E acetate | 0.50 | | 0.25 | | 1.00 |
| Alpha-glucosilrutin | | 0.60 | | | 0.25 |
| Fucogel ® 1000 | | 2.50 | 0.50 | | 2.00 |
| DMDM hydantoin | | 0.60 | 0.40 | 0.20 | |
| Glycacil-S ® | 0.20 | | | | |
| Methylparaben | 0.50 | | 0.25 | 0.15 | |
| Phenoxyethanol | 0.50 | 0.40 | | 1.00 | |
| Trisodium EDTA | | 0.01 | 0.05 | | 0.10 |
| Ethanol | 3.00 | 2.00 | 1.50 | | 7.00 |
| Perfume | 0.20 | | 0.05 | 0.40 | |
| Water | ad 100 | ad 100 | ad 100 | ad 100 | ad 100 |

| 3. W/O Sunscreen Emulsions | | | | | |
|---|---|---|---|---|---|
| | 1 | 2 | 3 | 4 | 5 |
| Cetyl dimethicone copolyol | | 2.50 | | 4.00 | |
| Polyglyceryl-2-dipolyhydroxystearate | 5.00 | | | | 4.50 |
| PEG-30-dipolyhydroxystearate | | | 5.00 | | |
| Aminobenzophenone | 3.50 | 4.00 | 5.00 | 1.50 | 0.25 |
| Ethylhexyl methoxycinnamate | | 8.00 | | 5.00 | 4.00 |

-continued

3. W/O Sunscreen Emulsions

| | 1 | 2 | 3 | 4 | 5 |
|---|---|---|---|---|---|
| Bis-ethylhexyloxyphenol methoxyphenyl triazine | 2.00 | 2.50 | | 2.00 | 2.50 |
| Butyl methoxy-dibenzoylmethane | | | 1.50 | | 0.70 |
| Disodium phenyl dibenzimidazole tetrasulfonate | | 1.00 | | 2.00 | 2.00 |
| Ethylhexyl triazone | | | 3.00 | 4.00 | |
| Octocrylene | 10.00 | | 7.50 | | 2.50 |
| Diethylhexyl butamido triazone | 1.00 | | | 2.00 | |
| Phenylbenzimidazole sulfonic acid | 0.50 | | | 3.00 | 2.00 |
| Methylene bis-benzotriazolyl tetramethylbutyl phenol | | 0.50 | 2.00 | | |
| Drometrizole trisiloxane | | 1.00 | | | 1.50 |
| Terephthalidene dicamphorsulfonic acid | | | 1.00 | | 0.50 |
| Diethylhexyl-2,6-naphthalate | 7.50 | 5.50 | 6.00 | 10.00 | 15.00 |
| Titanium dioxide T805 | | 2.00 | | | 3.00 |
| Titanium dioxide MT-100Z | | | 1.50 | | |
| Zinc oxide Z-Cote HP1 | 1.00 | | | 8.00 | 2.00 |
| Mineral oil | | 12.00 | 10.0 | | 8.00 |
| C12–15 Alkyl benzoate | | | | 9.00 | |
| Dicaprylyl ether | 10.00 | | | | 7.00 |
| Butylene glycol dicaprylate/dicaprate | | | 2.00 | 8.00 | 4.00 |
| Dicaprylyl carbonate | 5.00 | | 6.00 | | |
| Dimethicone | | 4.00 | 1.00 | 5.00 | |
| Cyclomethicone | 2.00 | 25.00 | | | 2.00 |
| Shea butter | | | 3.00 | | |
| Vaseline | | 4.50 | | | |
| PVP hexadecene copolymer | 0.50 | | | 0.50 | 1.00 |
| Ethylhexyl glycerin | | 0.30 | 1.00 | | 0.50 |
| Glycerin | 3.00 | 7.50 | | 7.50 | 8.50 |
| Glycine soy | | 1.00 | 1.50 | | 1.00 |
| MgSO₄ | 1.00 | 0.50 | | 0.50 | |
| MgCl₂ | | | 1.00 | | 0.70 |
| Vitamin E acetate | 0.50 | | 0.25 | | 1.00 |
| Ascorbyl palmitate | 0.50 | | | 2.50 | |
| Fucogel ®1000 | | | | 3.50 | 7.50 |
| DMDM hydantoin | | 0.60 | 0.40 | 0.20 | |
| Methylparaben | 0.50 | | 0.25 | 0.15 | |
| Phenoxyethanol | 0.50 | 0.40 | | 1.00 | |
| Trisodium EDTA | 0.12 | 0.05 | | 0.30 | |
| Ethanol | 3.00 | | 1.50 | | 5.00 |
| Perfume | 0.20 | | 0.40 | 0.35 | |
| Water | ad 100 | ad 100 | ad 100 | ad 100 | ad 100 |

4. Solids-stabilized Emulsions

| | 1 | 2 | 3 | 4 | 5 |
|---|---|---|---|---|---|
| Mineral oil | | | 16.0 | 16.0 | |
| Octyldodecanol | 9.0 | 9.0 | 5.0 | | |
| Caprylic/capric triglyceride | 9.0 | 9.0 | 6.0 | | |
| C-12–15 Alkyl benzoate | | | | 5.0 | 8.0 |
| Butylene glycol dicaprylate/dicaprate | | | | | 8.0 |
| Dicaprylyl ether | 9.0 | | | 4.0 | |
| Dicaprylyl carbonate | | 9.0 | | | |

4. Solids-stabilized Emulsions

|  | 1 | 2 | 3 | 4 | 5 |
|---|---|---|---|---|---|
| Hydroxyoctacosanyl hydroxystearate | 2.0 | 2.0 | 2.0 | 2.0 | 1.5 |
| Disteardimonium hectorite | 1.0 | 0.75 |  | 0.5 | 0.25 |
| Cera Microcristallina + Paraffinum Liquidum |  | 0.35 |  |  | 5.0 |
| Hydroxypropyl methyl cellulose |  |  | 0.1 |  | 0.05 |
| Dimethicone |  |  |  |  | 3.0 |
| Aminobenzophenone | 3.0 | 5.0 | 1.5 | 5.5 | 0.75 |
| Butyl methoxydibenzoylmethane |  | 0.5 | 3.50 |  | 0.5 |
| Ethylhexyl methoxycinnamate | 6.0 |  |  |  | 3.0 |
| Diethylhexyl butamido triazone |  | 2.0 |  |  | 4.0 |
| Ethylhexyl triazone | 2.0 |  | 1.5 | 4.0 |  |
| Octocrylene |  | 7.5 | 10.0 |  |  |
| Methylene bis-benzotriazolyl tetramethylbutyl phenol | 0.5 |  |  | 2.0 |  |
| Drometrizole trisiloxane |  | 0.5 |  | 1.0 |  |
| Terephthalidene dicamphorsulfonic acid |  | 1.0 | 0.5 |  | 1.50 |
| Disodium phenyl dibenzimidazole tetrasulfonate | 2.50 |  | 3.1 |  |  |
| Titanium dioxide + alumina + simethicone + aqua |  | 2.0 | 4.0 | 2.0 | 4.0 |
| Titanium dioxide + trimethoxycaprylylsilane | 4.0 |  |  |  | 3.0 |
| Zinc oxide Z-Cote HP1 | 2.5 |  |  | 6.0 |  |
| Silica dimethyl silylate |  |  | 1.0 |  |  |
| Boron nitride | 2.0 |  |  |  |  |
| Starch/sodium metaphosphate polymer |  | 0.5 |  |  |  |
| Diethylhexyl-2,6-naphthalate | 5.0 | 7.0 | 8.5 | 3.0 | 4.5 |
| Tapioca starch |  |  |  | 1.0 |  |
| Sodium chloride | 1.0 | 1.0 | 1.0 | 1.0 | 1.0 |
| Glycerin | 5.0 | 10.0 | 3.0 | 6.0 | 10.0 |
| Trisodium EDTA | 1.0 | 1.0 |  | 1.0 |  |
| Methylparaben |  |  |  |  | 0.2 |
| Propylparaben |  |  |  |  |  |
| Phenoxyethanol |  |  | 0.4 | 0.4 | 0.5 |
| Hexamidine diisethionate |  |  |  |  | 0.08 |
| Diazolidinyl urea |  |  | 0.28 | 0.28 |  |
| Alcohol | 5.0 |  |  | 2.5 |  |
| Perfume | 0.25 |  | 0.4 | 0.1 |  |
| Water | ad 100 | ad 100 | ad 100 | ad 100 | ad 100 |

5. Sticks

|  | 1 | 2 | 3 | 4 |
|---|---|---|---|---|
| Caprylic/capric triglyceride | 12 | 10 | 6 |  |
| Octyldodecanol | 7 | 14 | 8 | 3 |
| Butylene glycol dicaprylate/dicaprate |  |  |  | 12 |
| Pentaerythrityl tetraisostearate | 10 | 6 | 8 | 7 |
| Polyglyceryl-3 diisostearate | 2.5 |  |  |  |
| Bis-diglyceryl polyacyladipate-2 | 9 | 8 | 10 | 8 |
| Cetearyl alcohol | 8 | 11 | 9 | 7 |
| Myristyl myristate | 3.5 | 3 | 4 | 3 |
| Beeswax | 5 | 5 | 6 | 6 |
| Cera carnauba | 1.5 | 2 | 2 | 1.5 |
| Cera alba | 0.5 | 0.5 | 0.5 | 0.5 |
| C16–40 Alkyl stearate |  | 1.5 | 1.5 | 1.5 |
| Diethylhexyl-2,6-naphthalate | 5.5 | 13.0 | 2.5 | 8.0 |
| Aminobenzophenone | 2.0 | 5.5 | 1.0 | 0.5 |
| Butyl methoxydibenzoylmethane |  | 1 | 1 |  |
| Z-Cote ® HP1 |  |  |  | 4.5 |
| MT-100 TV |  |  | 4 | 2.5 |
| Titanium dioxide T 805 |  | 3.6 |  | 5 |
| Ethylhexyl methoxycinnamate | 3 | 3.6 |  | 2.5 |

5. Sticks

|  | 1 | 2 | 3 | 4 |
|---|---|---|---|---|
| Bis-ethylhexyloxyphenol methoxyphenyl triazine | 2.5 |  |  | 5 |
| Octocrylene |  |  | 7.5 |  |
| Benzophenone-3 |  |  | 3.5 |  |
| Ethylhexyl triazone | 2 |  |  |  |
| Diethylhexyl butamido triazone |  |  |  | 3 |
| Tocopheryl acetate | 0.5 | 1 |  |  |
| Ascorbyl palmitate | 0.05 |  | 0.05 |  |
| Buxus Chinensis | 2 | 1 |  | 1 |
| Perfume, BHT | 0.1 | 0.25 |  | 0.35 |
| Ricinus Communis | ad 100 | ad 100 | ad 100 | ad 100 |

5. PIT Emulsions

|  | 1 | 2 | 3 | 4 | 5 | 6 | 7 | 8 |
|---|---|---|---|---|---|---|---|---|
| Glycerin | 0.50 | 2.00 | 3.00 | 5.00 |  |  | 0.50 | 4.00 |
| monostearate SE |  |  |  |  |  |  |  |  |
| Glyceryl isostearate |  |  |  |  | 3.50 | 4.00 | 2.00 |  |
| Isoceteth-20 |  | 0.50 |  |  | 2.00 |  |  |  |
| Ceteareth-12 |  | 5.00 |  | 1.00 |  |  |  | 3.50 |
| Ceteareth-20 |  |  |  | 2.00 |  | 2.50 | 3.00 |  |
| PEG-100 stearate | 5.00 |  | 1.00 |  | 1.00 |  |  | 0.50 |
| Cetyl alcohol | 2.50 | 1.00 |  | 1.50 |  | 0.50 | 1.50 |  |
| Cetyl palmitate |  |  |  | 0.50 |  | 1.00 |  |  |
| Cetyl dimethicone copolyol | 0.50 |  |  |  | 0.50 |  | 1.00 |  |
| Polyglyceryl-2 Dipolyhydroxy stearate |  |  |  | 0.75 | 0.25 |  |  |  |
| Diethylhexyl-2,6-naphthalate | 7.00 | 3.50 | 8.00 | 6.00 | 15.0 | 4.00 | 5.00 | 4.50 |
| Aminobenzophenone | 2.00 | 3.00 | 1.00 | 1.50 | 5.00 | 3.00 | 0.75 | 2.50 |
| Bis-ethylhexyl-oxyphenol methoxy-phenyl triazine |  |  | 0.50 | 2.00 |  | 3.00 |  |  |
| Butyl methoxy-dibenzoylmethane | 1.50 |  | 1.00 |  | 5.00 | 1.00 | 0.75 |  |
| Disodium phenyl dibenzimidazole tetrasulfonate |  | 2.00 |  |  | 1.00 |  |  |  |
| Terephthalidene dicamphor sulfonic acid |  |  | 0.50 |  |  |  | 1.00 |  |
| Drometrizole trisiloxane |  |  | 2.00 |  |  | 3.00 |  | 1.00 |
| Ethylhexyl methoxycinnamate | 8.00 |  |  | 4.50 | 5.00 | 8.00 |  |  |
| Ethylhexyl salicylate | 4.00 |  |  |  | 3.50 | 4.00 |  |  |
| Dioctyl butamido triazone |  |  |  | 3.00 | 2.00 | 2.00 |  | 1.50 |
| Ethylhexyl triazone |  |  | 2.00 | 4.00 |  |  | 1.50 | 3.00 |
| Dimethicone diethylbenzalmalonate |  | 4.50 |  |  | 3.50 |  |  |  |
| Octocrylene |  |  | 5.00 |  | 8.00 | 10.0 |  | 7.50 |
| Phenylbenzimidazole sulfonic acid | 1.00 | 5.00 |  | 3.00 |  |  |  |  |
| C12–15 Alkyl benzoate | 3.50 |  |  |  | 6.50 |  |  |  |
| Cocoglycerides |  | 3.00 |  | 3.00 |  |  |  | 3.50 |
| Dicaprylyl ether | 4.00 |  |  |  |  |  |  |  |
| Butylene glycol dicaprylate/dicaprate |  | 4.00 |  | 3.00 |  |  |  |  |
| Dicaprylyl carbonate |  |  |  | 0.50 |  |  |  | 6.00 |
| Dibutyl adipate |  |  | 2.50 |  |  |  |  | 1.00 |
| Phenyltrimethicone | 2.00 |  |  | 3.00 |  |  |  |  |

| -continued | | | | | | | | |
|---|---|---|---|---|---|---|---|---|
| 5. PIT Emulsions | | | | | | | | |
| | 1 | 2 | 3 | 4 | 5 | 6 | 7 | 8 |
| Cyclomethicone | | 3.00 | | | | | | 4.00 |
| Ethyl galactomannan (N-Hance ® AG-200) | | 0.50 | | | 2.00 | | | |
| Hydrogenated cocoglycerides | | | | 3.00 | 4.00 | | | 2.50 |
| Abil ® Wax 2440 | | | | | | 1.50 | 3.00 | |
| PVP hexadecene copolymer | | | | 1.00 | 1.50 | | | |
| Glycerin | 10.0 | 5.00 | | 7.50 | | 10.00 | | |
| Fucogel ®1000 | | | 2.50 | 6.00 | | | | |
| Tocopherol | 1.00 | | | 0.75 | 0.50 | | 1.00 | |
| Shea butter | | 2.00 | 3.50 | | | | | 0.50 |
| Iodopropyl butyl-carbamate | 0.12 | | | | 0.20 | | | |
| DMDM hydantoin | | | | 0.10 | | | | |
| Methylparaben | | 0.50 | 0.25 | | 0.45 | | | |
| Phenoxyethanol | 0.50 | 0.40 | | 1.00 | | | | 1.00 |
| Octoxyglycerin | | 0.30 | | | 1.00 | 0.35 | | |
| Ethanol | | | | 2.00 | | 6.00 | 7.50 | 4.00 |
| Trisodium EDTA | | 0.40 | | 0.15 | | 0.20 | | 0.50 |
| Perfume | 0.20 | | 0.20 | 0.20 | 0.45 | | | 0.20 |
| Water | ad 100 | ad 100 | ad 100 | ad 100 | ad 100 | ad 100 | ad 100 | ad 100 |

The invention claimed is:

1. Light-protective cosmetic or dermatological preparation, comprising:

(a) at least one hydroxybenzophenone of the following structural formula:

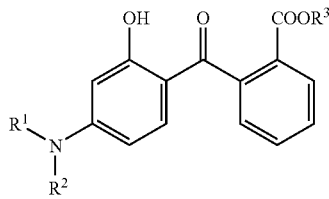

where

R¹ and R² independent of one another are hydrogen, $C_1$–$C_{20}$-alkyl, $C_3$–$C_{10}$-cycloalkyl or $C_3$–$C_{10}$-cyloalkenyl, wherein the substituents R¹ and R² together with the nitrogen atom to which they are bound can form a 5- or 6-ring, and R³ is a $C_1$–$C_{20}$ alkyl radical, and (b) at least one dialkyl naphthalate comprising the structural formula

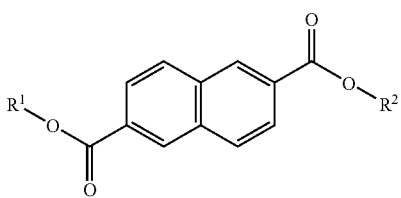

where R¹ and R² are independently one of branched and unbranched alkyl groups with 6 to 24 carbon atoms.

2. Light-protective cosmetic or dermatological preparation, comprising synergistic substance combinations of (a) at least one hydroxybenzophenone of the following structural formula:

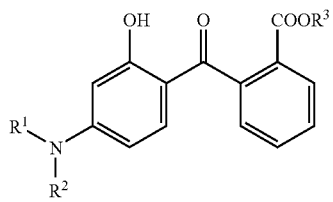

where

R¹ and R² independent of one another are hydrogen, $C_1$–$C_{20}$-alkyl, $C_3$–$C_{10}$-cycloalkyl or $C_3$–$C_{10}$-cyloalkenyl, wherein the substituents R¹ and R² together with the nitrogen atom to which they are bound can form a 5- or 6-ring, and R³ is a $C_1$–$C_{20}$ alkyl radical, and (b) at least one dialkyl naphthalate comprising the structural formula

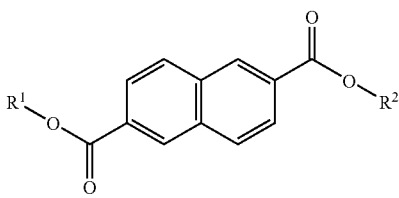

where R¹ and R² are independently one of branched and unbranched alkyl groups with 6 to 24 carbon atoms, wherein UV protective effect, in particular UVA protective effect, of the preparation is higher than that of the same preparation that does not contain any substances according to (b).

3. Preparation according to claim 1, wherein the at least one dialkyl naphthalate is present in a range of from 0.001 to 30% by weight relative to the total weight of the preparation.

4. Preparation according to claim 1, comprising at least one further UV filter substance comprising at least one of triazines, benzotriazoles, liquid UV filter substances and at least one of organic and inorganic pigments.

5. Preparation according to claim 1, comprising at least one further UVA filter substance and/or a broadband filter comprising at least one of dibenzoylmethane derivatives and 2,4-bis{[4-(2-ethylhexyloxy)-2-hydroxy]phenyl}-6-(4-methoxyphenyl)-1,3,5-triazine.

6. Preparation according to claim 1, comprising at least one of at least one flavone glycoside and vitamin E and/or derivatives thereof.

7. A method of moistening skin comprising applying a preparation according to claim 1 on the skin.

8. A method of protecting skin against light-related aging of the skin comprising applying a preparation according to claim 1 on the skin.

9. A method of achieving or increasing solubility of at least one hydroxybenzophenone comprising combining said at least one hydroxybenzophenone, the at least one hydroxybenzophenone having the following structural formula:

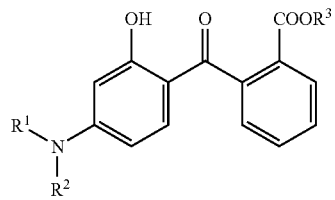

where $R^1$ and $R^2$ independent of one another are hydrogen, $C_1$–$C_{20}$-alkyl, $C_3$–$C_{10}$- cycloalkyl or $C_3$–$C_{10}$-cyloalkenyl, wherein the substituents $R^1$ and $R^2$ together with the nitrogen atom to which they are bound can form a 5- or 6-ring, and $R^3$ is a $C_1$–$C_{20}$ alkyl radical, and with at least one dialkyl naphthalate comprising the structural formula

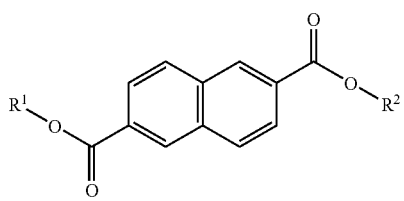

where $R^1$ and $R^2$ are independently one of branched and unbranched alkyl groups with 6 to 24 carbon atoms.

10. A method of stabilizing dibenzoylmethane derivatives in cosmetic or dermatological preparations against decomposition that is induced by UV radiation comprising including combinations of (a) at least one hydroxybenzophenone of the following structural formula:

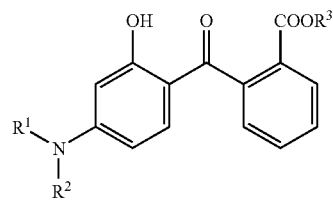

where $R^1$ and $R^2$ independent of one another are hydrogen, $C_1$–$C_{20}$-alkyl, $C_3$–$C_{10}$-cycloalkyl or $C_3$–$C_{10}$-cyloalkenyl, wherein the substituents $R^1$ and $R^2$, together with the nitrogen atom to which they are bound can form a 5- or 6-ring, and $R^3$ is a $C_1$–$C_{20}$ alkyl radical, and (b) at least one dialkyl naphthalate of the structural formula

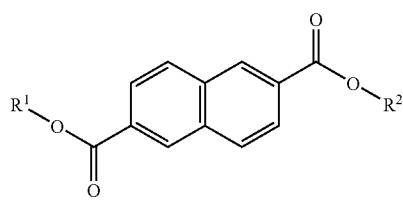

where $R^1$ and $R^2$ are independently one of branched and unbranched alkyl groups with 6 to 24 carbon atoms, in a cosmetic or dermatological preparation containing dibenzoylmethane derivatives in an amount effective to stabilize the dibenzoylmethane derivatives against the decomposition that is induced by UV radiation.

11. Preparation according to claim 3, wherein the at least one dialkyl naphthalate is present in a range of from 0.01 to 20% by weight relative to the total weight of the preparation.

12. Preparation according to claim 11, wherein the at least one dialkyl naphthalate is present in a range of from 0.5 to 15% by weight relative to the total weight of the preparation.

13. Preparation according to claim 5, wherein said dibenzoylmethane derivatives comprise 4-(tert-butyl)-4'- methoxydibenzoylmethane].

14. Preparation according to claim 1, wherein the at least one flavone glycoside comprises α-glucosylrutin.

15. Preparation according to claim 2, wherein the at least one dialkyl naphthalate is present in a range of from 0.001 to 30% by weight-relative to the total weight of the preparation.

16. Preparation according to claim 2, comprising at least one further UV filter substance comprising at least one of triazines, benzotriazoles, liquid UV filter substances and at least one of organic and inorganic pigments.

17. Preparation according to claim 2, comprising at least one further UVA filter substance and/or a broadband filter comprising at least one of dibenzoylmethane derivatives and 2,4-bis{[4-(2-ethylhexyloxy)-2-hydroxy]phenyl}-6-(4-methoxyphenyl)-1,3,5-triazine.

18. Preparation according to claim 2, comprising at least one of at least one flavone glycoside and vitamin E and/or derivatives thereof.

19. Preparation according to claim 5, comprising at least one further UVA filter substance and/or a broadband filter comprising at least one of dibenzoylmethane derivatives and 2,4-bis{[4-(2-ethylhexyloxy)-2-hydroxy]phenyl}-6-(4-methoxyphenyl)-1,3,5-triazine.

20. Preparation according to claim 4, comprising at least one of at least one flavone glycoside and vitamin E and/or derivatives thereof.

* * * * *